United States Patent [19]

Ruger et al.

[11] Patent Number: 5,223,139
[45] Date of Patent: Jun. 29, 1993

[54] FILTER MATERIAL IN THE FORM OF FLEXIBLE LEAVES OR SHEETS AND A METHOD OF PRODUCING SUCH MATERIAL

[75] Inventors: Helmut Ruger, Pfaffen-Schwabenheim; Gerd Ritter, Guldental; Hans Hofmann, Hargesheim; Peter Breitbach, Bretzenheim, all of Fed. Rep. of Germany

[73] Assignee: Seitz-Filter-Werke Theo & Geo Seitz GmbH & Co., Bad Kreuznach, Fed. Rep. of Germany

[21] Appl. No.: 506,667

[22] Filed: Apr. 9, 1990

[30] Foreign Application Priority Data

Apr. 11, 1989 [DE] Fed. Rep. of Germany ....... 3911825

[51] Int. Cl.⁵ ............................................. B01D 39/02
[52] U.S. Cl. .................................. 210/505; 210/508; 210/509; 55/527; 162/157.5
[58] Field of Search .................. 210/505, 508, 509; 55/527; 162/139, 157.5

[56] References Cited

U.S. PATENT DOCUMENTS

| | | |
|---|---|---|
| 3,842,007 | 10/1974 | Caputi, Jr. et al. |
| 4,110,385 | 8/1978 | Sander et al. ............ 162/157.5 |
| 4,548,677 | 10/1985 | Schneider et al. ............ 162/139 |
| 4,565,727 | 1/1986 | Giglia et al. ............ 210/505 |
| 4,650,506 | 3/1987 | Barris et al. ............ 210/505 |
| 4,925,560 | 5/1990 | Sorrick ............ 210/505 |
| 4,976,858 | 12/1990 | Kadaya ............ 210/505 |

FOREIGN PATENT DOCUMENTS

| | | |
|---|---|---|
| 1561753 | 3/1972 | Fed. Rep. of Germany . |
| 2444947 | 3/1975 | Fed. Rep. of Germany . |
| 2801685 | 7/1978 | Fed. Rep. of Germany . |
| 2910289 | 9/1980 | Fed. Rep. of Germany . |
| 3329385 | 2/1985 | Fed. Rep. of Germany . |
| 4010526 | 10/1990 | Fed. Rep. of Germany . |

*Primary Examiner*—Robert A. Dawson
*Assistant Examiner*—W. L. Millard
*Attorney, Agent, or Firm*—H. Gibner Lehmann; K. Gibner Lehmann

[57] ABSTRACT

A flexible fleece-like filter material is provided wherein in a matrix-like basic framework consisting of synthetic or natural fibres, ultra-finely fibrillated fibres and/or inert porous particles are incorporated as a filter medium, the filter medium forming, anchored in the matrix, chain structures provided with a cationic or anionic charge or possibly charged with other substances which influence the filtering properties or with immobilised cells and/or catalysts. A fleece is formed with a thickness of between 0.5 mm and 5 mm and preferably up to 2 mm, which is flexible and which can even be pleated. This filter material can be produced by a simple method without harming the environment.

14 Claims, 3 Drawing Sheets

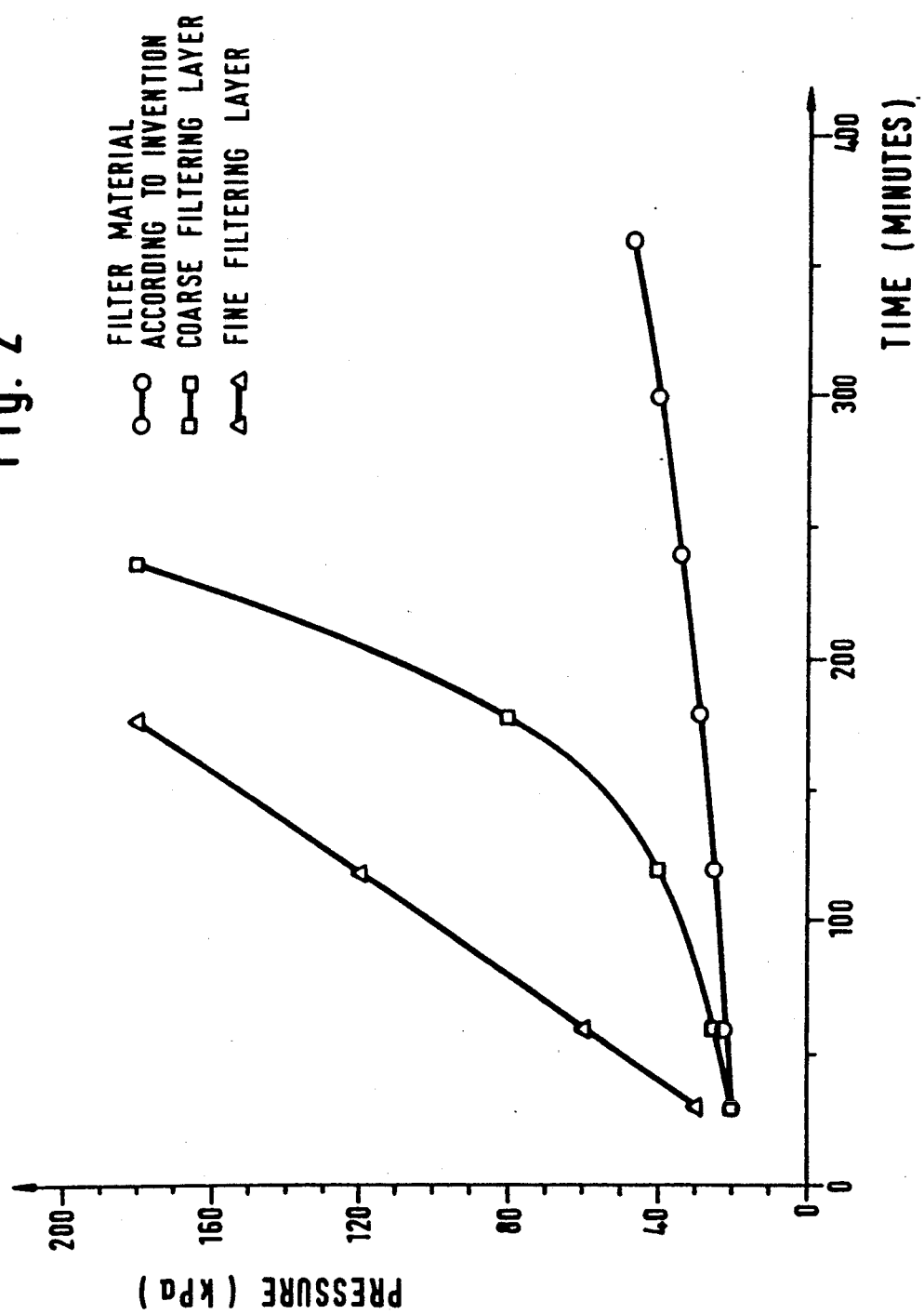

FILTER MATERIAL IN THE FORM OF FLEXIBLE LEAVES OR SHEETS AND A METHOD OF PRODUCING SUCH MATERIAL

Description

The invention relates to a filter material constructed from a framework of synthetic and/or natural fibres with an incorporated filter medium which retains impurities.

Filter material of this basic structure has been previously known in the form of rigid panels or filter layers for use as deep filter material or deep dead filter material, preferably being used in filter presses and similar filtering equipment. It cannot however be used for those applications in which special shaping is involved or when there is more or less marked deformation of the filter material when it is installed into a filter unit or a filter element.

DE-AS 15 61 753 does indeed describe a strip-like or web-like two-layer filter material comprising a thin bottom layer of substantially denser structure and consisting of fibre material and a coarsely structured layer of fibres, the fibres in the thin bottom layer being orientated in the surface of the layer while in the coarsely structured layer they are orientated at right-angles to the surface of the layer. Cohesion of the fibres in the layers, particularly in the coarsely structured layer, is achieved by a resin binder. This filter material can indeed be flexible and constructed to a relatively small thickness but it only has deep filtering properties, if at all, to a very minor degree.

In contrast, the object of the invention is to make available a flexible pliant filter material which can be adapted to any geometrical form and, after the fashion of a deep filter fleece, has the same characteristics of separating impurities as do the prior art deep filter layers, while exceeding these by having a substantially better capacity for regeneration than to the known deep filter layers.

According to the invention, this problem is resolved by the filter material being constructed in the form of flexible leaves or sheets of fleece-like structure in the combination
a) of a basic framework in the form of a matrix consisting of self-binding synthetic and/or natural fibres which are at least partially fibrillated and which are ground down to a degree of 5° to 50° SR, with
b) incorporated into the basic framework a filter medium of very finely fibrillated fibrous material and/or inert particles, the filter medium at least partially forming a fine three-dimensional chain structure anchored in the matrix of the basic framework.

By virtue of their minimal thickness and flexibility, the filter fleeces according to the invention can be pleated, i.e. laid in an undulating pattern or even rolled up and are thus suitable for processing in filter elements which can be used for filtering clouded or colloidally laden media and/or for the selective separation of substances from a solution.

In a preferred embodiment of the invention, the basic framework may consist of a mixture of polyolefin fibres and/or pure wood-pulp, preferably coniferous wood-pulp and/or cotton fibres, the mixture being fibrillatingly ground down to 5° to 50° by a wet process.

In a preferred embodiment, the filter medium may contain 0 to 4% by weight coniferous wood-pulp and/or cotton fibres which are very finely and fibrillatingly ground by a wet process to a degree of preferably 50° to $\geq 90°$ SR and/or very fine synthetic fibres, preferably cellulose acetate fibres. The fibres of filter medium can thereby be blended with 0 to 4% by weight (related to the solids) of a retention agent, e.g. polyethylene imine normally used in the paper-making industry and diluted with a solvent.

The filter medium may furthermore contain 0 to 70% by weight inert particles with a clearly defined particle size of between 0.5 and 100 um. The inert particles of filter medium may consist of agglomerate particles, preferably agglomerate particles of precipitating silicic acid or such agglomerate particles. The filter medium—particularly if it has inert particles - may contain 0 to 4% by weight retention agent, for example polyamine.

Against extraction, substances which produce physical and/or chemical changes may be reliably bonded on the surface of the fibrillated fibres and/or agglomerate particles of the filter medium. In this way, the electrically uncharged components are during the production process cationically or anionically charged by means of a retention agent. It is also possible to bond immobilized cells and/or enzymes on the surface of the very finely fibrillated fibres and/or particles of agglomerate in the filter medium. According to the particular application for which the filter material is intended, so also selected biocatalysts can be bonded on the surface of the fibrillated fibres and/or agglomerate particles of the filter medium.

To strengthen the filter material additionally, other plastics may be introduced into the filter material to effect additional cross-linking. Such plastics may preferably be polyacrylates. These plastics are added to the finished mash which already contains the retention agent to obtain an appropriate flocculation. The percentage of these cross-linkable plastics ranges from more than 0 to 10% percent by weight, relative to the entire filter material.

In addition to the flexible and reliably processable and deformable construction in the form of 0.5 mm to 5 mm fleece-like leaves or sheets, a particular advantage of the fleece-like material according to the invention resides in the fact that despite its flexible construction, this filter material is in its filtering properties by no means inferior to the deep filter layers and can furthermore, due to its composition according to the invention, be substantially better regenerated than the previous deep filter layers. Further advantages of the filter material according to the invention reside in the fact that all its above-mentioned contents are in principle low in ions or are ion-free AOX-free and free from other organic pollutants, in other words they comply with exacting demands of purity.

The filter fleeces according to the invention can be produced in various pore sizes and have different adsorption properties. At the same time, there is the possibility of combining such filter fleeces of different pore sizes and different adsorption properties when producing filter elements.

In order to produce the filter material according to the invention, there is one particularly suitable method which is characterised by the following procedural steps:
a) The basic structure of the filter material is formed by synthetic fibres and/or natural fibres which are able to form a self-binding matrix and are fibrillatingly ground to 5° to 50° SR by a wet method;

b) 0 to 40% by weight (related to the solids content) of fibres of a coniferous wood-pulp and/or cotton fibres and/or synthetic fibres, preferably cellulose acetate fibres, ground by a wet process to a degree of grind of 50° up to ≧90° SR and/or 0 to 70% by weight (related to the solids content) porous inert particles, partially in the form of agglomerate particles and preferably precipitating silicic acid, are admixed with the fibrous substance/fluids mixture formed by grinding the fibres which form the basic framework;

c) the mash formed by this blending process is then formed by a per se known felting process to produce a fleece 0.5 mm to 5 mm thick which is then dried.

This method of manufacture can be carried out easily and in an environmentally-protective manner. In terms of adding further constituents and with regard to the conduct of the process, it can within wide limits be adapted to special demands in order to obtain a filter material with a fleece structure as the product of the process which can cope with any desired special filtration tasks. In a further development of the method according to the invention, it is possible to add to the mixture of ground fibres of the basic framework with filter medium 0 to 4% by weight (related to the solids contents) of retention agent in a 1 to 5% and preferably in a 1% solution, a substance such as polyamine for example.

The fibres of filter medium which have to be added to the mixture of ground fibres of the basic framework and of diluent may be finely ground down to 50° to ≧90° SR and immediately after this grinding process, with 0 to 4% by weight (in relation to the solids content) of a retention agent in 1% to 5% and preferably in a 1% dilution, preferably polyethylene imine, may be added so that the fibres are electrically reverse-charged.

In the method according to the invention, the porous inert particles which have to be added to the mixture of ground fibres of the basic framework with diluent and which have an agglomerate particle size of 0.5 to 100 μm can be fixed, 0.4% by weight (in relation to the solids content) of retention agent in a 1% to 5% and preferably in a 1% dilution, being added to the resultant mixture.

Furthermore, in the method according to the invention, the porous inert particles and/or fine fibres which have to be blended with the mixture of ground fibres of the basic framework and of the diluent may, prior to being admixed, be subject to the action of cationic and-/or anionic polymers or copolymers and/or substances which produce physical or chemical changes, these polymers or copolymers and/or substances being, by means of a per se known immobilising process, reliably bonded on the surface of the particles or fibres to preclude extraction.

In the method according to the invention and in the case of the filter material according to the invention, synthetic fibres other than those mentioned above may be considered.

During the processing of the mash to form filter material, it is possible according to the invention for the completed mash to be formed into a fleece by the application of a vacuum.

In the accompanying drawings:

FIG. 2 shows the turbidity retention capacity of the filter material according to the invention.

Examples of embodiment:

Manufacture of a deep filter fleece in the "fine clarification range"

Figure 1:
FIG. 1 shows a greatly enlarged view of an embodiment of the filter material according to the invention.

54.75% polypropylene fibres (Hercules PAD fibres) and 5% polyethylene fibres (ESS 21 fibres from the Schwarzwälder Textile Works) are blended together briefly and intensively with a refiner to form a basic framework 1 (see structural sketch, FIG. 1), after which 30% silicic acid (FK 310-precipitating silicic acid by Degussa) are added which, prior to admixture, has been deagglomerated by a dispersing process so that with the or without the very finely fibrillatingly ground fibres 2, preferably ground down to a degree between 50° and ≧90° SR, a three-dimensional chain structure is formed. In addition 10% finely fibrillatingly ground coniferous wood-pulp 2 ground to about 80° SR are admixed and 0.25% retention agent (polyimine PL from Messrs. BASF) is slowly added with agitation. Then, the polyolefin fibres are likewise added slowly but with intense agitation and, by means of a vacuum felting method, formed into an approx. 1.5 mm thick sheet and dried at 150° C. As FIG. 1 shows, the silicic acid particles form agglomerates (3) in a chain structure. The sheet can then be rolled up and used for example as a filter active fleece in a cartridge.

Filtration examples:

Comparisons were drawn with asbestos-free filter layers which belong to the prior art.

Where the filtration examples are concerned, the same effective filter areas were employed.

1. Filtration of coffee liquor solution containing yeast and used as a sample liquid. The throughput was constantly 800 $l \times m^{-2} \times h^{-1}$. As a measure of the turbidity absorption capacity, the clarification effect was ascertained using a commercially available turbidity meter.

See FIG. 2: Pressure/time

2. Filtration of a raw cane sugar solution with hot water regeneration against the direction of flow. The throughput was a constant 1000 $l\, m^{-2}h^{-1}$.

As a measure of the turbidity absorption capacity, the unfiltered and filtered materials were measured with a commercially available turbidity meter.

Figure 3A:
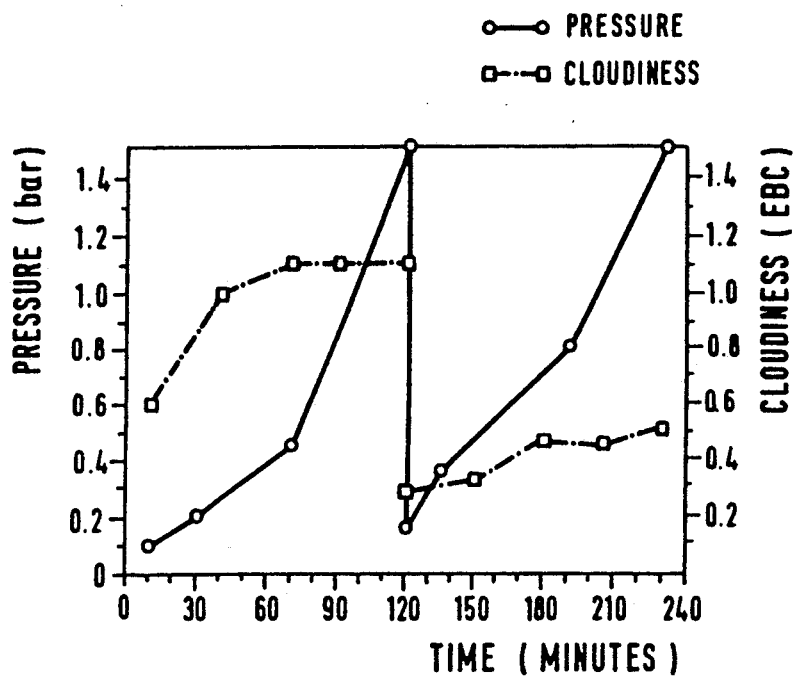
FIGS. 3a and 3b show the filtering action of filter material according to the invention (FIG. 3a) with the filtration action of the combination of a conventional finely clarifying filter layer (FIG. 3b) in the filtering of a raw sugar cane solution.
Figure 3B:
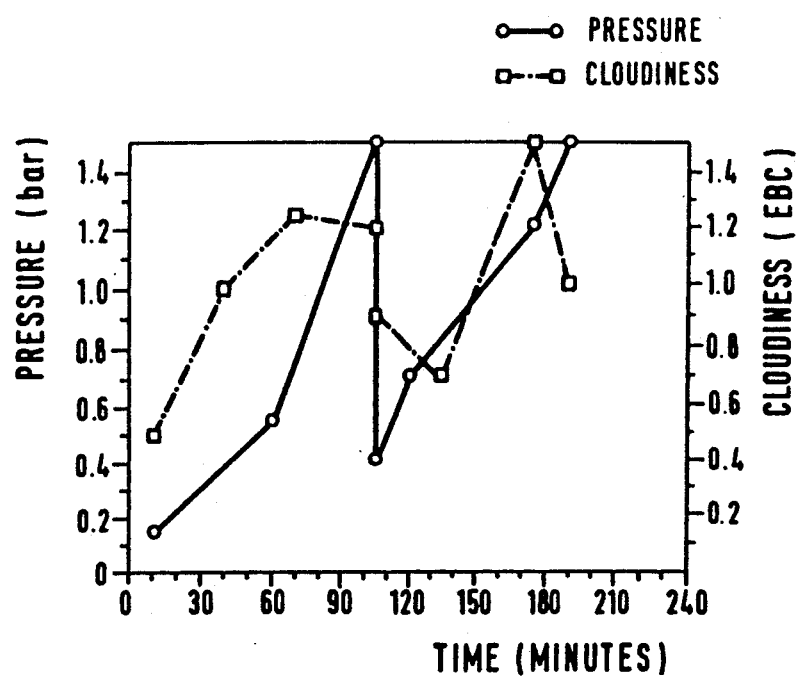

See FIG. 3a: Time/pressure/clouding-FIG. 3a for filter material according to the invention and Time/pressure/clouding-FIG. 3b for a finely clarifying filter layer

We claim:

1. Filter material in the form of flexible leaves or sheets having a fleece-like structure and adapted for use as a deep-bed filter for filtration of liquid, comprising in combination:

a) a basic internal framework in the form of a matrix consisting of self-binding fibres which are at least partially fibrillated and which are ground down to between 5° and 50° SR, and b) a filter medium incorporated into the said framework, said filter medium being adapted to retain impurities from said liquid, said filter medium being constituted of material selected from the group consisting of finely fibrillated fibres and inert particles, said inert particles having a particle size of between 0.5 and 100 μm., said filter medium at least partially forming a fine spatial chain structure anchored in the matrix of the basic framework.

2. Filter material according to claim 1, wherein the fibres of the filter medium are blended with up to 4% by weight of a retention agent.

3. Filter material according to claim 2, wherein said retention agent comprises polyethylene imine diluted with a solvent.

4. Filter material according to claim 2, wherein the retention agent comprises polyamine.

5. Filter material according to claim 1, wherein the filter material contains cross-linkable plastics for mechanical strengthening.

6. Filter material according to claim 5, wherein the cross-linkable plastics comprise polyacrylates.

7. Filter material according to claim 1, wherein the basic framework comprises a mixture of fibrous materials selected from the group consisting of polyolefin fibres, wood-pulp fibres, and cotton fibres, said fibrous materials being fibrillatingly ground down to between 5° and 50° SR by means of a wet process.

8. Filter material according to claim 1, wherein said filter medium contains between 0 and 40% by weight, a substance selected from the group consisting of coniferous wood-pulp and cotton fibres and synthetic fibres, said substance being finely fibrillatingly ground by a wet process to a degree of from 50° to greater than or equal to 90° SR.

9. Filter material according to claim 1, wherein the filter medium consists of inert particles of agglomerate which is derived by precipitating silicic acid.

10. Filter material according to claim 1, wherein the filter medium comprises inert particles of agglomerate, and wherein immobilized material selected from the group consisting of immobilized cells and enzymes are deposited on the surface of the particles of agglomerate.

11. Filter material according to claim 1, wherein the filter medium comprises immobilized material selected from the group consisting of immobilized cells and enzymes and said immobilized material is deposited on the surface of the fibrillated fibres.

12. Filter material according to claim 1, wherein the filter medium comprises inert particles of agglomerate, and wherein material selected from the group consisting of immobilized cells and biocatalysts is deposited on the surface of the particles of agglomerate.

13. Filter material according to claim 1, wherein the filter medium comprises material selected from the group consisting of immobilized cells and biocatalysts, and said material of the group is deposited on the surface of the finely fibrillated fibres.

14. Filter material according to claim 1, wherein said filter medium contains between 0 and 40% by weight, cellulose acetate fibres, very finely fibrillatingly ground by a wet process to a degree of from 50° to greater than or equal to 90° SR.

* * * * *